United States Patent
Wang et al.

(10) Patent No.: US 11,094,059 B2
(45) Date of Patent: Aug. 17, 2021

(54) VULNERABLE PLAQUE IDENTIFICATION METHOD, APPLICATION SERVER THEREOF, AND COMPUTER READABLE MEDIUM

(71) Applicant: PING AN TECHNOLOGY (SHENZHEN) CO., LTD., Guangdong (CN)

(72) Inventors: Jianzong Wang, Guangdong (CN); Tianbo Wu, Guangdong (CN); Lihong Liu, Guangdong (CN); Xinhui Liu, Guangdong (CN); Jing Xiao, Guangdong (CN)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 38 days.

(21) Appl. No.: 16/633,153

(22) PCT Filed: Jun. 12, 2018

(86) PCT No.: PCT/CN2018/090905
§ 371 (c)(1),
(2) Date: Jan. 22, 2020

(87) PCT Pub. No.: WO2019/140857
PCT Pub. Date: Jul. 25, 2019

(65) Prior Publication Data
US 2020/0202519 A1 Jun. 25, 2020

(30) Foreign Application Priority Data
Jan. 18, 2018 (CN) .......................... 201810047424.1

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0066* (2013.01); *A61B 5/02007* (2013.01);
(Continued)

(58) Field of Classification Search
CPC ..................... G06T 7/0012; G06T 7/73; G06T 2207/10101; G06T 2207/20081;
(Continued)

(56) References Cited

U.S. PATENT DOCUMENTS

2008/0228086 A1* 9/2008 Llegbusi ............... A61B 5/0075
600/479
2012/0242835 A1* 9/2012 Li ....................... G06K 9/00798
348/148
(Continued)

FOREIGN PATENT DOCUMENTS

CN 106780495 * 5/2017 .......... A61B 5/0066
CN 106780495 A 5/2017
(Continued)

OTHER PUBLICATIONS

Bin Liu, ("Study Of Object Detection Based On Faster R-CNN", College of Automation & Electronic Engineering Qingdao University of Science and Technology Qingdao, China, IEEE 2017, pp. 6233-6236) (Year: 2017).*
(Continued)

*Primary Examiner* — Amara Abdi (57) ABSTRACT

The present disclosure publishes a vulnerable plaque identification method. The method includes: receiving an angiocarpy image sent by a terminal device; transforming the angiocarpy image in an original Cartesian coordinate system into a polar coordinate system to form a polarization image; constructing a faster RCNN architecture and accomplishing a training; inputting the polarization image into the faster RCNN architecture accomplished the training to identify the
(Continued)

polarization image, and outputting the image with the marked vulnerable plaques; feed backing the image with the marked vulnerable plaques to the terminal device. The present disclosure also publishes an application server and a computer readable medium. The vulnerable plaque identification method, the application server, and the computer readable medium can quickly and correctly conform the position of the vulnerable plaque.

12 Claims, 6 Drawing Sheets

(51) Int. Cl.
*G06T 7/73* (2017.01)
*G16H 30/40* (2018.01)
*A61B 5/00* (2006.01)
*A61B 5/02* (2006.01)

(52) U.S. Cl.
CPC .............. *G06T 7/73* (2017.01); *G16H 30/40* (2018.01); *A61B 2576/00* (2013.01); *G06T 2207/10101* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC . G06T 2207/20084; G06T 2207/30048; G06T 2207/30101; G06T 3/0012; G06T 2207/20104; G16H 30/40; G16H 40/63; G16H 50/20; A61B 5/0066; A61B 5/02007; A61B 2576/00

See application file for complete search history.

(56) References Cited

U.S. PATENT DOCUMENTS

| | | | | |
|---|---|---|---|---|
| 2015/0281544 | A1* | 10/2015 | Joo | G06T 5/008 382/131 |
| 2018/0089536 | A1* | 3/2018 | Feng | G06K 9/00805 |
| 2019/0125307 | A1* | 5/2019 | Unger | A61B 5/0095 |

FOREIGN PATENT DOCUMENTS

| | | |
|---|---|---|
| JP | 2003240727 A | 8/2003 |
| JP | 2017537768 A | 12/2017 |
| WO | 2017214421 A1 | 12/2017 |

OTHER PUBLICATIONS

Bhavani Sambaturu et al., A Novel Deep Learning Based Method for Retinal Lesion Detection, 2017 International Conference on Advances in Computing, Communications and Informatics (ICACCI), Sep. 13, 2017, pp. 33-37, IEEE, USA.

Mengdi Xu et al., Automatic Image Classification in Intravascular Optical Coherence Tomography Images, 2016 IEEE Region 10 Conference (TENCON), Nov. 22, 2016, pp. 1544-1547, IEEE, USA.

Shaoqing Ren et al., Faster R-CNN: Towards Real-Time Object Detection with Region Proposal Networks, Advances in Neural Information Processing System 28 (NIPS 2015), Dec. 7, 2015, pp. 1-11, NeurIPS, Canada.

Zhang, Qi, Medical Image Processing in Atherosclerosis Research, Wanfang Data, Dec. 2012, pp. ii, 5, 43-44, 61-62, 80, 83.

Dong, Lanfang et al., Face Detection Using the Faster R-CNN Method, Computer Systems & Applications, Dec. 2017, pp. 264-266, vol. 26, No. 12.

* cited by examiner

VULNERABLE PLAQUE IDENTIFICATION METHOD, APPLICATION SERVER THEREOF, AND COMPUTER READABLE MEDIUM

CROSS-REFERENCE TO RELATED APPLICATION

The present application claims priority to Chinese Patent Application No. 201810047424.1 entitled "VULNERABLE PLAQUE IDENTIFICATION METHOD, APPLICATION SERVER THEREOF, AND COMPUTER READABLE MEDIUM" filed on Jan. 18, 2018, the contents of which is expressly incorporated by reference herein in its entirety.

TECHNICAL FIELD

The present disclosure relates the field of medical image analysis, and specially relates to a vulnerable plaque identification method, an application server thereof, and a computer readable medium.

BACKGROUND

Coronary heart disease has become a first reason of human death. In America, a death rate of the coronary heart disease has already been higher than a sum of death rates of all cancer, which becomes a first reason of death. A pathological basis caused the coronary heart disease is coronary atherosclerosis. Plaques in blood vessel caused by coronary atherosclerosis has a certain unstable, these plaques can also be called as vulnerable plaques, and the unstable plaques cause a rupture of the blood vessel, bleeding, thrombus, therefore various blood vessel diseases are caused. In China, the death of the cardiovascular diseases is on the top of the total death reason, and the number of morbidity person is increased by years, which threaten the health of the people in China. A traditional method for identifying the vulnerable plaques in the OCT image of the angiocarpy is implemented by taking partial of the fibrous plaque and a partial of the non-fibrous plaque as a test sample, and analysing a position of the vulnerable plaques, but this identification manner takes a long time and the accuracy does not reach the expect object.

SUMMARY OF THE INVENTION

The present disclosure involves a vulnerable plaque identification method, an application server thereof, and a computer readable medium, aiming to improve the recited problem.

Firstly, to achieve the aim, the present disclosure provides a vulnerable plaque identification method. The vulnerable plaque identification method includes:

Receiving an angiocarpy image sent by a terminal device;
Transforming the angiocarpy image in an original Cartesian coordinate system into a polar coordinate system to form a polarization image;
Constructing a faster RCNN architecture and accomplishing a training;
Inputting the polarization image into the faster RCNN architecture accomplished the training to identify the polarization image, and outputting the image with the marked vulnerable plaques;
Feed backing the image with the marked vulnerable plaques to the terminal device.

Besides, to achieve the aim, the present disclosure provides an application server, including a storage and a processor; the storage stores a vulnerable plaques identification system executed in the processor; the vulnerable plaque identification system being executed by the processor includes the following steps:

Receiving an angiocarpy image sent by a terminal device;
Transforming the angiocarpy image in an original Cartesian coordinate system into a polar coordinate system to form a polarization image;
Constructing a faster RCNN architecture and accomplishing a training;
Inputting the polarization image into the faster RCNN architecture accomplished the training to identify the polarization image, and outputting the image with the marked vulnerable plaques;
Feed backing the image with the marked vulnerable plaques to the terminal device.

Further, to achieve the aim, the present disclosure provides a computer readable medium, the computer readable medium stores a vulnerable plaque identification system; the vulnerable plaque identification system is executed by at least one processor, for causing the at least one processor to execute the steps of the recited vulnerable plaque identification method.

By comparing with the related art, the vulnerable plaque identification method, the application server, and the computer readable medium of the present disclosure firstly receive an angiocarpy image sent by a terminal device; then transform the angiocarpy image in an original Cartesian coordinate system into a polar coordinate system to form a polarization image; further construct a faster RCNN architecture and accomplish a training; further input the polarization image into the faster RCNN architecture accomplished the training to identify the polarization image and output the image with the marked vulnerable plaques, feed back the image with the marked vulnerable plaques to the terminal device at last, thus the doctors can quickly and correctly conform the position of the vulnerable plaques based on the image with the marked vulnerable plaques.

BRIEF DESCRIPTION OF THE FIGURES

Implementations of the present disclosure will now be described, by way of example only, with reference to the attached figures, wherein.

DETAILED DESCRIPTION

In order to make the technical problems, the technical solutions, and beneficial effects to be clearer and more understand, the present disclosure is further described in detail with reference to the accompanying drawings and the embodiments. It will be understood that the specific embodiments described herein are merely used for describing the present disclosure, but are not intended to limit the present disclosure. Based on the present disclosure, any other embodiments obtained by persons skilled in the art without creative effort shall all fall into the protection scope of the present disclosure.

It needs to be explained that the descriptions related to "first", "second" and so on in the present disclosure are only description purpose, but are not being understood as indicating or implying a relative significance of itself or implying an amount of the indicated technical feature. Thus, the features limited with "first" or "second" are indicated or implied including at least one feature. Besides, the technical solutions between different embodiments can be mutual combination, but only based on being achieved by those of an ordinary skill in the art, it should be recognized that the technical solution is not existed when the combination of the technical solutions being mutual contradiction or being unable to be achieved, and it is also not within the protecting range of the present disclosure.

Figure 1:
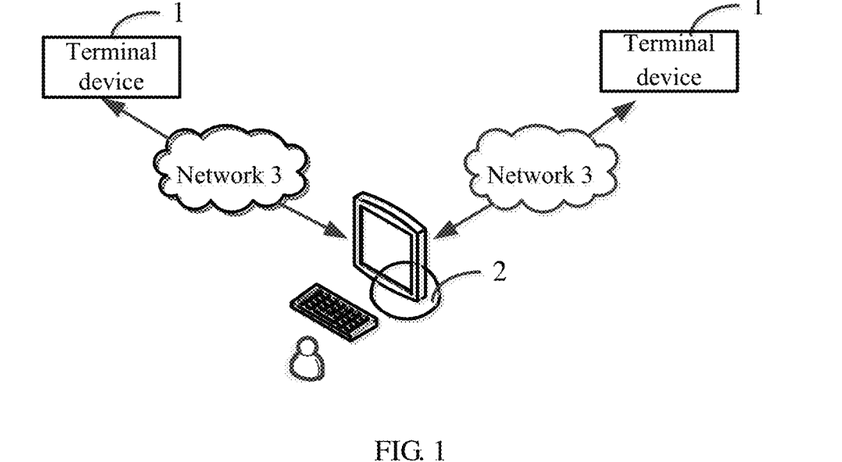
FIG. 1 is a diagram view of each embodiment of an optional application environment.

As shown in FIG. 1, it is an application environment of each embodiment of the present disclosure.

In one embodiment, the present disclosure is applied to an application environment including, but not limiting, a terminal device 1, an application server 2, and a network 3. The terminal device 1 can be a medical scan device, such as a computerized tomography device, a nuclear paramagnetic resonance device, a X-ray machines, and so on. The application server 2 can be a computer device, such as a rack-mounted server, a blade server, a tower server, a cabinet server, and so on. The network 3 can be a wired network or a wireless network, such as Intranet, Internet, Global System of Mobile communication (GSM), Wideband Code Division Multiple Access (WCDMA), 4G network, 5G network, Bluetooth, Wi-Fi, phone network, and so on.

The application server 2 is communicated with the one or more terminal device 1 through the network 3 for transferring and interacting data.

In one embodiment, the terminal device 1 includes the terminal device 1 corresponding a hospital.

Figure 2:
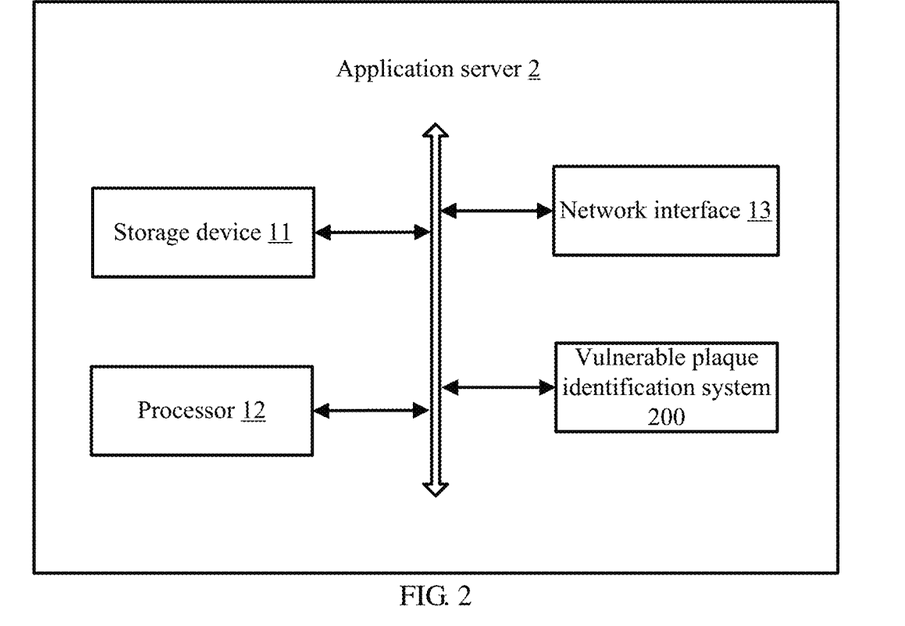
FIG. 2 is a diagram view of an embodiment of an optional hardware construction of the application server in FIG. 1.

FIG. 2 shows a diagram view of an optional hardware structure of the application server 2.

In one embodiment, the application server 2 can include, but not limiting, a storage device 11, a processor 12, and a network interface 13, which communicates with each other through a system bus. It needs to be noted that, FIG. 1 only shows the application server 2 including the components 11-13, but it should be understood that the shown components are not being required to be implemented, less or more components can be replaced implemented.

The application server 2 can be a computer device, such as a rack-mounted server, a blade server, a tower server, a cabinet server, and so on. The application server 2 can be an independent server or a server cluster including multiple servers.

The storage device 11 includes at least one type of readable storage medium. The readable storage medium can include a flash memory, a hard disk, multi-media card, a card type storage (for example, a SD or a DX storage), a read-access memory (RAM), a static read-access memory (SRAM), a read-only memory (ROM), an electrically programmable read-only memory (EEPROM), a programmable read-only memory (PROM), a magnetic memory, a magnetic disk, or an optical disk. In some embodiments, the storage device 11 can be an internal storage unit of the application server 2, such as a hard disk of the application server 2. In other embodiments, the storage device 11 can be an external storage device of the application server 2, such as a plug-in hard disk, a smart media card (SMC), a secure digital (SD) card, or a flash card. Certainly, the storage device 11 also can include the internal storage unit of the application server 2, and also include the external storage device of the application server 2. In one embodiment, the storage device 11 usually stores an operating system and various types of software of the application server 2, such as program codes of the vulnerable plaque identification system 200 in the embodiment of the present disclosure, and so on. Besides, the storage device 11 also temporarily stores various to-be-outputted or outputted data.

The processor 12, in some embodiment, can be a central processing unit (CPU), a controller, a micro controller, a micro processor, or any other data processing chip. The processor 12 usually controls a general operation of the application server 2. In the present disclosure, the processor 12 is used for running the programming code stored in the storage device 11 or processing the data, such as the vulnerable plaque identification system 200, and so on.

The network interface 13 can include a wireless network interface or a wired network interface. The network interface 13 is usually used for establishing a communication connection between the application server 2 and other electric devices.

At this point, the related hardware structures and the functions of the present disclosure have already explained. As below, different embodiments of the present disclosure are introduced based on the above description.

Firstly, the present disclosure provides a vulnerable plaque identification 200.

Figure 3:
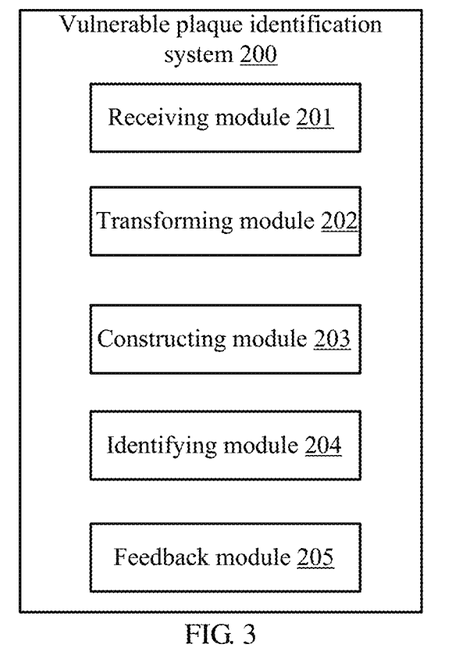
FIG. 3 is a diagram view of a first embodiment of a vulnerable plaque identification system of the present disclosure.

FIG. 3 shows a diagram view of a first embodiment of the vulnerable plaque identification system 200 of the present disclosure.

In one embodiment, the vulnerable plaque identification system 200 includes a series of computer instructions stored in the storage device 11. The computer instructions are capable of being implemented by the processor 12 for achieving a vulnerable plaque identification operation of each embodiment of the present disclosure. In some embodiments, the computer instructions are divided into different logic modules based on the executed specified operations of different parts of the computer instructions. The vulnerable plaque identification system 200 can be divided into one or more modules. For example, in FIG. 3, the vulnerable plaque identification system 200 can be divided into a receiving module 201, a transforming module 202, a constructing module 203, an identifying module 204, and a feedback module 205.

The receiving module 201 is configured to receive an angiocarpy image sent by the terminal device 1.

In detail, the angiocarpy image is an optical coherence tomography (OCT) image. The application server 2 establishes a long connection with the terminal device 1. In one embodiment, the terminal device 1 is an OCT photography equipment. When the angiocarpy OCT image captured by the terminal device 1, the angiocarpy OCT image is transmitted to the application server 2. The application server 2 receives the angiocarpy OCT image through the receiving module 201.

The transforming module 202 is configured to transform the angiocarpy OCT image in an original Cartesian coordinate system into a polar coordinate system to form a polarization image.

In detail, the application server 2 pre-processes the angiocarpy OCT image through the transforming module 202, and marks proposal regions of the angiocarpy OCT image. In one embodiment, the angiocarpy are marked as the proposal regions.

Figure 4:
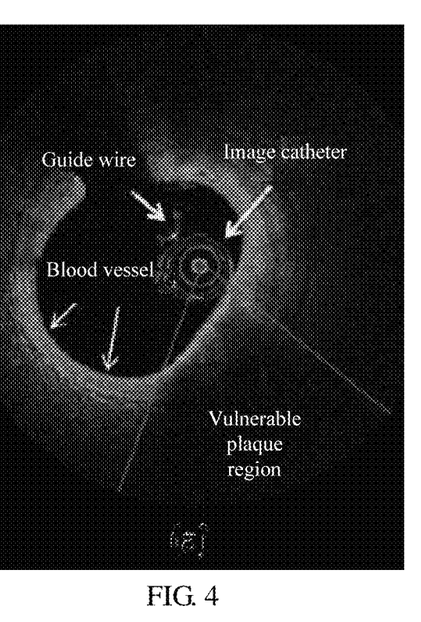
FIG. 4 is a diagram view of the OCT image of the present disclosure.

Referring to FIG. 4 together, FIG. 4 shows an embodiment of the angiocarpy OCT image of the present disclosure. As shown in FIG. 4, the application server 2 identifies the angiocarpy regions as the proposal regions through the transforming module 202. The identification process is a common image identification in medicinal, it will not repeat here. The red regions in FIG. 4 are proposal regions, the transforming module 202 transforms the proposal regions in the original Cartesian coordinate system into the polar coordinate system to form the polarization image.

Figure 5:
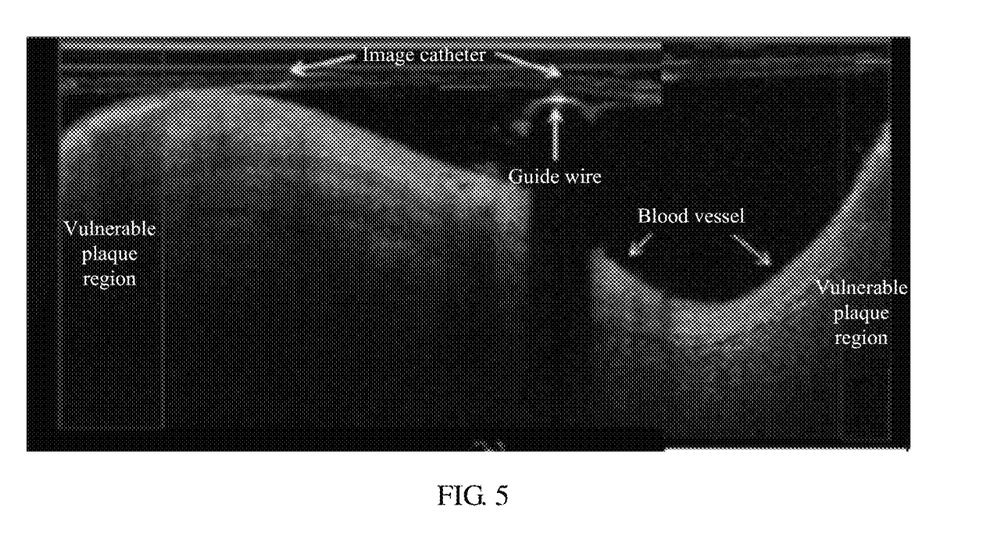
FIG. 5 is a diagram view of the polarization OCT image of the present disclosure.

Referring to FIG. 5 together, FIG. 5 shows an embodiment of the angiocarpy OCT the polarization image of the present disclosure. By transforming, the proposal regions in a sector shape in FIG. 4 is expended into a rectangular shape, which makes the vulnerable plaques in the angiocarpy OCT image to be identified more easily.

The constructing module 203 is configured to construct a faster region-based convolutional neural network (RCNN) architecture and accomplish a training.

In one embodiment, the detail process of constructing the faster RCNN architecture and accomplishing the training is: extracting features of the polarization image to form feature image, generating proposal region frames on the feature image by nine anchors on different combinations of three different areas and three different ratios; extracting features in the proposal region frames for achieving locations and deep features of the vulnerable plaques.

Figure 6:
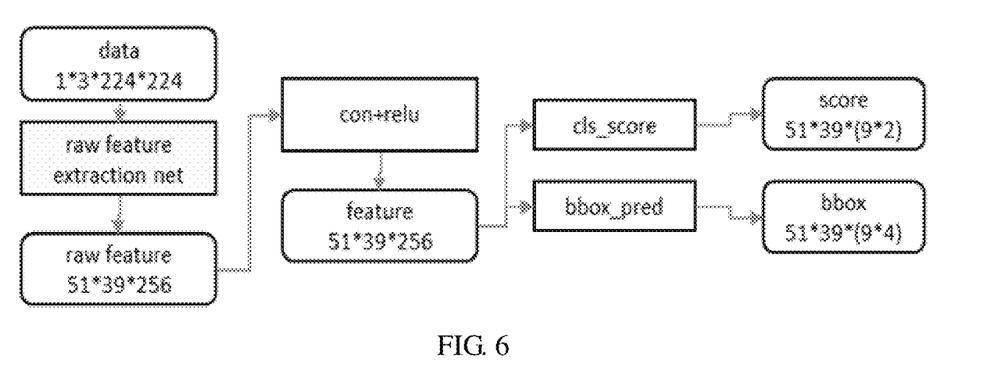
FIG. 6 is a diagram view of an embodiment of the Faster RCNN architecture of the present disclosure.

Referring to FIG. 6 together, FIG. 6 shows an embodiment of the faster RCNN architecture of the present disclosure. The faster RCNN architecture includes multiple convolution layers and multiple rectified linear unit (RELU) layers, which is a common classification architecture of an ImageNet. An extra convolution layer and an extra RELU layer are added for outputting 51*39*256 dimensional features. Each feature can be considered as 256 channel images in a 51*39 scale. Each location in the channel image considers nine possibility proposal windows called as the anchors. A set of the three areas is $\{128^2, 256^2, 512^2\}$, and a set of the three ratios is $\{1:1, 1:2, 2:1\}$. Probabilities belonging to a foreground or a background of the nine anchors of each location are outputted by a classification score layer. Translating and scaling parameters of the nine anchors of each location are outputted by a bounding box predict layer.

To each location, the classification score layer outputs the probabilities belonging to the foreground or the background from the 256 dimensional features, and the bounding box predict layer outputs four translating and scaling parameters from the 256 dimensional features.

The identifying module 204 inputs the polarization image into the faster RCNN architecture accomplished the training, identifies the polarization image, and outputs the image with the marked vulnerable plaques.

In detail, as shown in FIG. 4, while the application server 2 pre-processes the image, which is transformed the angiocarpy OCT image in the original Cartesian coordinate system into the polar coordinate system, the vulnerable plaque adjacent to zero point is divided into two parts, it go against to detect an object. For getting rid of this problem, in one embodiment, the application server 2 copies and connects the polarization image in a horizontal manner, which cause the vulnerable plaques to be reconnected a complete region in the image, thus the polarization image being complete connected is inputted into the RCNN architecture after being trained, for identifying the polarization image and outputting the image with the marked vulnerable plaques.

The feedback module 205 feed backs the image with the marked vulnerable plaques to the terminal device.

In detail, the application server 2 feed backs the image with the marked vulnerable plaques to a display interface of the terminal device through the feedback module 205, doctors can quickly and correctly conform the position of the vulnerable plaques according to the image with the marked vulnerable plaques.

By the program modules 201-205, the vulnerable plaques identification system 200 in present disclosure firstly receives the angiocarpy image from the terminal device; then transforms the angiocarpy image in an original Cartesian coordinate system into a polar coordinate system to form a polarization image; further constructs a faster RCNN architecture and accomplishing a training; inputs the polarization image into the faster RCNN architecture accomplished the training to identify the polarization image, and outputs the image with the marked vulnerable plaques; lastly feed backs the image with the marked vulnerable plaques to the terminal device, thus the doctors can quickly and correctly conform the position of the vulnerable plaques according to the image with the marked vulnerable plaques.

Figure 7:
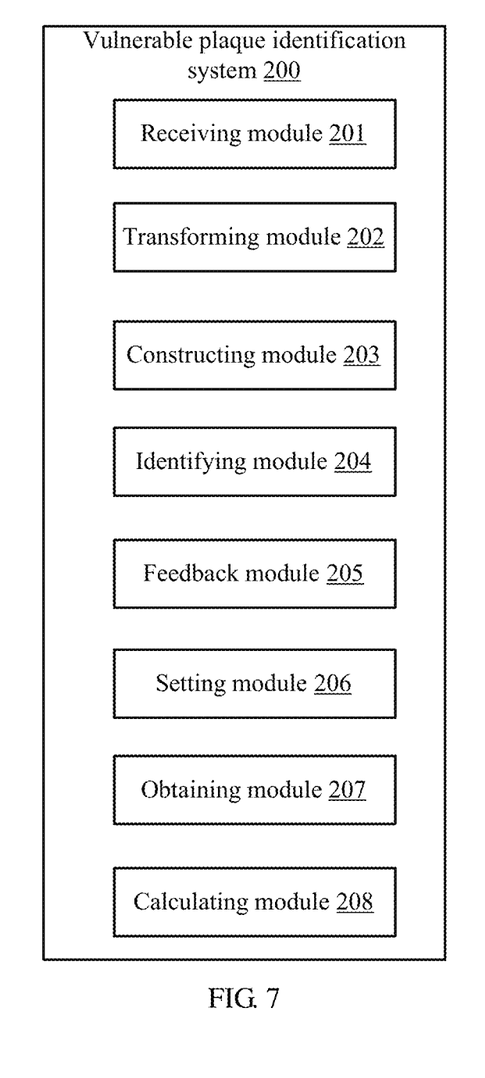
FIG. 7 is a diagram view of a second embodiment of a vulnerable plaque identification system of the present disclosure.

Referring to FIG. 7, FIG. 7 is a diagram view of a second embodiment of a vulnerable plaques identification system 200. In one embodiment, the vulnerable plaque identification system 200 includes the receiving module 201, the transforming module 202, the constructing module 203, the identifying module 204, and the feedback module 205 in the first embodiment, also includes a setting module 206, an obtaining module 207, and a calculating module 208.

The setting module 206 sets a centre of the angiocarpy image as an origin, and also sets an anticlockwise direction as a positive direction, and a direction below the positive direction of the origin as a direction of θ at 0 degree.

The obtaining module 207 obtains each pixel $T(\theta, \rho)$ in the angiocarpy image. θ represents an angle between the pixel and the positive direction, and ρ represents a distance between the pixel and the origin.

The calculating module 208 calculates coordinate values x, y of each pixel in the angiocarpy image under the polar coordinate system by formulas $x = \rho \cos \theta$, $y = \rho \sin \theta$.

In detail, the application server 2 considers the centre of the angiocarpy image as the origin, the direction below the positive direction of the origin as a direction of θ at 0 degree, the positive direction is an anticlockwise direction. Each pixel $T(\theta, \rho)$ in the angiocarpy image is traversed, θ represents an angle between the pixel and the positive direction, and ρ represents a distance between the pixel and the origin. By the formulas $x = \rho \cos \theta$, $y = \rho \sin \theta$, coordinate values x, y of each pixel in the angiocarpy image are calculated under the polar coordinate system. The new coordinate (x, y) is the location of the pixel $T(\theta, \rho)$ in the polar coordinate system. By traversing the whole image in this manner, the new image being expended is obtained. As shown in FIG. 4, by a form of expending the vulnerable plaque regions into a rectangular shape, the image can be easily processed and identified.

By the program modules 206-208, the vulnerable plaques identification system 200 in present disclosure further sets the a centre of the angiocarpy image as an origin, also set an anticlockwise direction as a positive direction and a direction below the positive direction of the origin as a direction of θ at 0 degree; obtains each pixel T(θ, ρ) in the angiocarpy image, in which θ represents an angle between the pixel and the positive direction, and ρ represents a distance between the pixel and the origin; calculates coordinate values x, y of each pixel in the angiocarpy image under the polar coordinate system by formulas x=ρ cos θ, y=ρ sin θ; thus the polarization image is obtained, by a form of expending the vulnerable plaque regions into a rectangular shape, the image can be easily processed and identified.

Besides, the present disclosure also provides a vulnerable plaques identification method.

Figure 8:
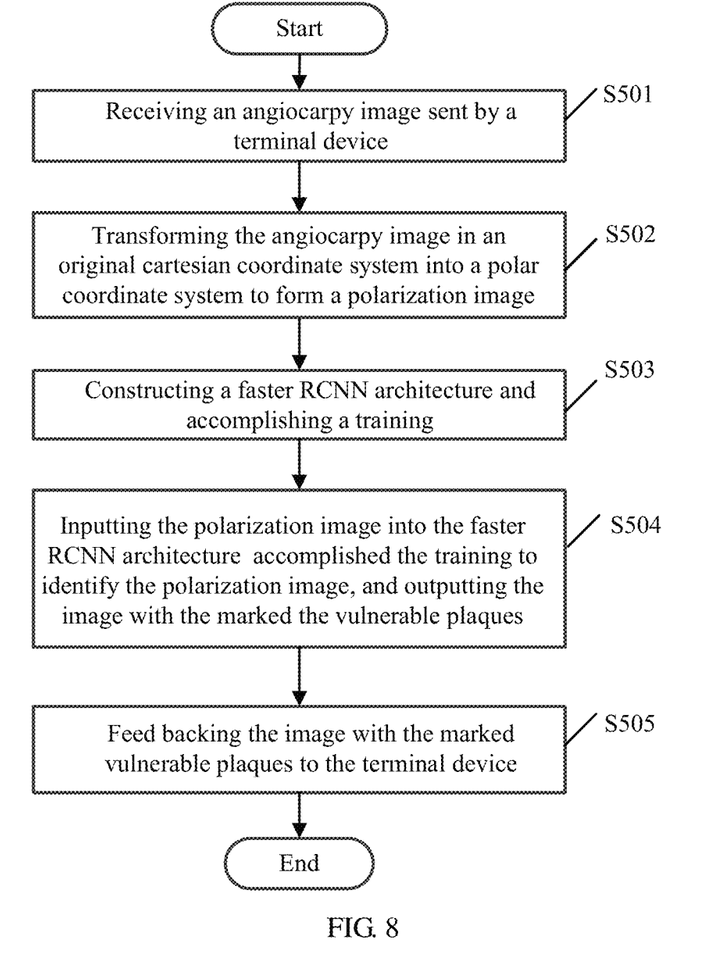
FIG. 8 is a flowchart of a first embodiment of a vulnerable plaque identification method of the present disclosure.

Referring to FIG. 8, FIG. 8 is a flowchart of a first embodiment of the vulnerable plaque identification method. In one embodiment, according different requirements, the steps in the FIG. 8 may be executed in a different sequence, and some steps can be omitted.

Step 501, receiving an angiocarpy image sent by a terminal device;

In detail, the angiocarpy image is an optical coherence tomography (OCT) image. The application server 2 establishes a long connection with the terminal device 1. In one embodiment, the terminal device 1 is an OCT photography equipment. When the angiocarpy OCT image captured by the terminal device 1, the angiocarpy OCT image is transmitted to the application server 2.

Step 502, transforming the angiocarpy image in an original Cartesian coordinate system into a polar coordinate system to form a polarization image;

In detail, the application server 2 pre-processes the angiocarpy OCT image through the transforming module 202, and marks proposal regions of the angiocarpy OCT image. In one embodiment, the angiocarpy are marked as the proposal regions.

Referring to FIG. 4 together, FIG. 4 shows an embodiment of the angiocarpy OCT image of the present disclosure. As shown in FIG. 4, the application server 2 identifies the angiocarpy regions as the proposal regions through the transforming module 202. The identification process is a common image identification in medicinal, it will not repeat here. The red regions in FIG. 4 are proposal regions, the transforming module 202 transforms the proposal regions in the original Cartesian coordinate system into the polar coordinate system to form the polarization image.

Referring to FIG. 5 together, FIG. 5 shows an embodiment of the angiocarpy OCT the polarization image of the present disclosure. By transforming, the proposal regions in a sector shape in FIG. 4 is expended into a rectangular shape, which makes the vulnerable plaques in the angiocarpy OCT image to be identified more easily.

Step 503, constructing a faster RCNN architecture and accomplishing a training;

In one embodiment, the detail process of constructing the faster RCNN architecture and accomplishing the training is: extracting features of the polarization image to form feature image, generating proposal region frames on the feature image by nine anchors on different combinations of three different areas and three different ratios; extracting features in the proposal region frames for achieving locations and deep features of the vulnerable plaques.

Referring to FIG. 6 together, FIG. 6 shows an embodiment of the faster RCNN architecture of the present disclosure. The faster RCNN architecture includes multiple convolution layers and multiple rectified linear unit (RELU) layers, which is a common classification architecture of an ImageNet. An extra convolution layer and an extra RELU layer are added for outputting 51*39*256 dimensional features. Each feature can be considered as 256 channel images in a 51*39 scale. Each location in the channel image considers nine possibility proposal windows called as the anchors. A set of the three areas is {1282,2562,5122}, and a set of the three ratios is {1:1,1:2,2:1}. Probabilities belonging to a foreground or a background of the nine anchors of each location are outputted by a classification score layer. Translating and scaling parameters of the nine anchors of each location are outputted by a bounding box predict layer.

To each location, the classification score layer outputs the probabilities belonging to the foreground or the background from the 256 dimensional features, and the bounding box predict layer outputs four translating and scaling parameters from the 256 dimensional features.

Step 504, inputting the polarization image into the faster RCNN architecture accomplished the training to identify the polarization image, and outputting the image with the marked vulnerable plaques;

In detail, as shown in FIG. 4, while the application server 2 pre-processes the image, which is transformed the angiocarpy OCT image in the original Cartesian coordinate system into the polar coordinate system, the vulnerable plaque adjacent to zero point is divided into two parts, it go against to detect an object. For getting rid of this problem, in one embodiment, the application server 2 copies and connects the polarization image in a horizontal manner, which cause the vulnerable plaques to be reconnected a complete region in the image, thus the polarization image being complete connected is inputted into the RCNN architecture after being trained, for identifying the polarization image and outputting the image with the marked vulnerable plaques.

Step 505, feed backing the image with the marked vulnerable plaques to the terminal device.

In detail, the application server 2 feed backs the image with the marked vulnerable plaques to a display interface of the terminal device through the feedback module 205, doctors can quickly and correctly conform the position of the vulnerable plaques according to the image with the marked vulnerable plaques.

By the steps of S501-S505, the vulnerable plaques identification method in present disclosure firstly receives the angiocarpy image from the terminal device; then transforms the angiocarpy image in an original Cartesian coordinate system into a polar coordinate system to form a polarization image; further constructs a faster RCNN architecture and accomplishing a training; inputs the polarization image into the faster RCNN architecture accomplished the training to identify the polarization image, and outputs the image with the marked vulnerable plaques; lastly feed backs the image with the marked vulnerable plaques to the terminal device, thus the doctors can quickly and correctly conform the position of the vulnerable plaques according to the image with the marked vulnerable plaques.

Figure 9:
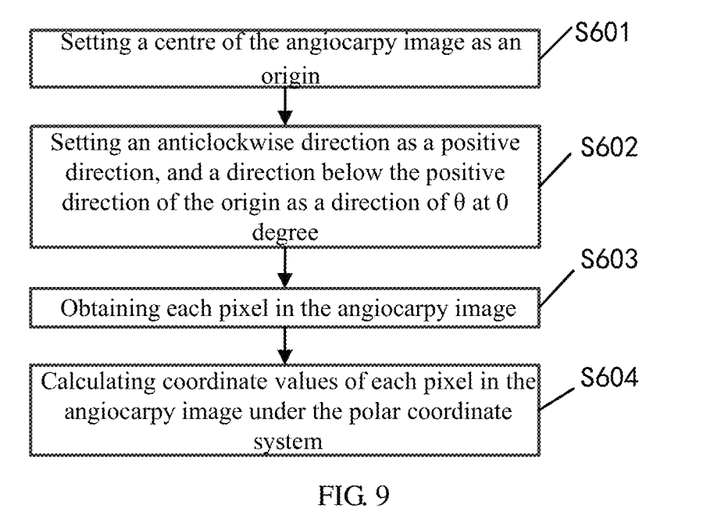
FIG. 9 is a flowchart of a second embodiment of a vulnerable plaque identification method of the present disclosure.

Referring to FIG. 9, FIG. 9 shows a flowchart of a second embodiment of a vulnerable plaque identification method. In one embodiment, the step of transforming the angiocarpy OCT image in an original Cartesian coordinate system into a polar coordinate system to form a polarization image specifically includes the following steps:

Step 601, setting a centre of the angiocarpy image as an origin;

Step 602, setting an anticlockwise direction as a positive direction, and a direction below the positive direction of the origin as a direction of θ at 0 degree.

Step 603, obtaining each pixel T(θ, ρ) in the angiocarpy image. θ represents an angle between the pixel and the positive direction, and ρ represents a distance between the pixel and the origin Step 604, calculating coordinate values x, y of each pixel in the angiocarpy image under the polar coordinate system by formulas x=ρ cos θ, y=ρ sin θ.

In detail, the application server 2 considers the centre of the angiocarpy image as the origin, the direction below the positive direction of the origin as a direction of θ at 0 degree, the positive direction is an anticlockwise direction. Each pixel T(θ, ρ) in the angiocarpy image is traversed, θ represents an angle between the pixel and the positive direction, and ρ represents a distance between the pixel and the origin. By the formulas x=ρ cos θ, y=ρ sin θ, coordinate values x, y of each pixel in the angiocarpy image are calculated under the polar coordinate system. The new coordinate (x, y) is the location of the pixel T(θ, ρ) in the polar coordinate system. By traversing the whole image in this manner, the new image being expended is obtained. As shown in FIG. 4, by a form of expending the vulnerable plaque regions into a rectangular shape, the vulnerable plaque regions can be easily processed and identified.

By the steps S601-604, the vulnerable plaque identification method in present disclosure further sets the a centre of the angiocarpy image as an origin, also set an anticlockwise direction as a positive direction and a direction below the positive direction of the origin as a direction of θ at 0 degree; obtains each pixel T(θ, ρ) in the angiocarpy image, in which θ represents an angle between the pixel and the positive direction, and ρ represents a distance between the pixel and the origin; calculates coordinate values x, y of each pixel in the angiocarpy image under the polar coordinate system by formulas x=ρ cos θ, y=ρ sin θ; thus the polarization image is obtained, by a form of expending the vulnerable plaque regions into a rectangular shape, the vulnerable plaque regions can be easily processed and identified.

The foregoing numbering of the embodiments of the disclosure is intended for description only, and is not indicative of the advantages and disadvantages of these embodiments.

By the description of the foregoing embodiments, it will be evident to those skilled in the art that the methods according to the above-mentioned embodiments can be implemented by means of software plus the necessary general-purpose hardware platform; and they can of course be implemented by hardware, but in many cases the former will be more advantageous. Based on such an understanding, the essential technical solution of the disclosure, or the portion that contributes to the prior art may be embodied as software products. Computer software products can be stored in a storage medium (e.g., a read-only memory (ROM)/random access memory (RAM), a magnetic disk, an optical disc), including multiple instructions that, when executed, can cause a computing device (e.g., a mobile phone, a computer, a server, a network device), to execute the methods described in the various embodiments of the disclosure.

The foregoing embodiments of the disclosure is a preferred embodiment, therefore are not intended as limiting the patentable scope of the disclosure. Equivalent structure or equivalent procedure change, which is directly or indirectly used in other related technical fields, are made using the content of the specification and the drawings of the disclosure shall all fall within the patentable scope of the disclosure.

What is claimed is:

1. A vulnerable plaque identification method, used in an application server, the method comprising:
receiving an angiocarpy image sent by a terminal device;
transforming the angiocarpy image in an original Cartesian coordinate system into a polar coordinate system to form a polarization image;
constructing a faster RCNN architecture and accomplishing a training;
inputting the polarization image into the faster RCNN architecture accomplished the training to identify the polarization image, and outputting the image with the marked vulnerable plaques; and
feed backing the image with the marked vulnerable plaques to the terminal device;
wherein the step of transforming the angiocarpy image in an original Cartesian coordinate system into a polar coordinate system to form a polarization image further comprising:
setting a centre of the angiocarpy image as an origin;
setting an anticlockwise direction as a positive direction, and a direction below the positive direction of the origin as a direction of θ at 0 degree;
obtaining each pixel T(θ,ρ) in the angiocarpy image; θ represents an angle between the pixel and the positive direction, and ρ represents a distance between the pixel and the origin; and
calculating coordinate values x, y of each pixel in the angiocarpy image under the polar coordinate system by formulas x=ρ cos θ, y=ρ sin θ.

2. The vulnerable plaque identification method of claim 1, wherein before the step of inputting the polarization image into the faster RCNN architecture accomplished the training to identify the polarization image further comprising:
copying and connecting the polarization image in a horizontal manner, which cause the vulnerable plaques to be reconnected a complete region in the image.

3. The vulnerable plaque identification method of claim 1, wherein the step of constructing a faster RCNN architecture and accomplishing a training comprising:
extracting features to form feature image;
generating proposal region frames on the feature image; and
extracting features in the proposal region frames to obtain locations and deep features of the vulnerable plaque.

4. The vulnerable plaque identification method of claim 3, wherein the step of forming anchors on the feature image comprising:
generating the proposal region frames by nine anchors on different combinations of three different areas and three different ratios.

5. An application server, wherein the application server comprises a storage and a processor, the storage stores a vulnerable plaque identification system executed in the processor; the vulnerable plaque identification system is executed by at least one processor for performing following steps:
receiving an angiocarpy image sent by a terminal device;
transforming the angiocarpy image in an original Cartesian coordinate system into a polar coordinate system to form a polarization image;
constructing a faster RCNN architecture and accomplishing a training;

inputting the polarization image into the faster RCNN architecture accomplished the training to identify the polarization image, and outputting the image with the marked vulnerable plaques; and feed backing the image with the marked vulnerable plaques to the terminal device;

wherein the step of transforming the angiocarpy image in an original Cartesian coordinate system into a polar coordinate system to form a polarization image further comprising:

setting a centre of the angiocarpy image as an origin;

setting an anticlockwise direction as a positive direction, and a direction below the positive direction of the origin as a direction of θ at 0 degree;

obtaining each pixel $T(θ,ρ)$ in the angiocarpy image; θ represents an angle between the pixel and the positive direction, and ρ represents a distance between the pixel and the origin; and calculating coordinate values x, y of each pixel in the angiocarpy image under the polar coordinate system by formulas $x=ρ \cos θ$, $y=ρ \sin θ$.

6. The application server of claim 5, wherein before the step of inputting the polarization image into the faster RCNN architecture accomplished the training to identify the polarization image further comprising:

copying and connecting the polarization image in a horizontal manner, which cause the vulnerable plaques to be reconnected a complete region in the image.

7. The application server of claim 5, wherein the step of constructing a faster RCNN architecture and accomplishing a training comprising:

extracting features to form feature image;

generating proposal region frames on the feature image; and extracting features in the proposal region frames to obtain locations and deep features of the vulnerable plaque.

8. The application server of claim 7, wherein the step of forming anchors on the feature image comprising:

generating the proposal region frames by the nine anchors on different combinations of three different areas and three different ratios.

9. A non-transitory computer readable medium, the computer readable medium stores a vulnerable plaque identification system; the vulnerable plaque identification system is executed by at least one processor, for causing the at least one processor to execute following steps:

receiving an angiocarpy image sent by a terminal device;

transforming the angiocarpy image in an original Cartesian coordinate system into a polar coordinate system to form a polarization image;

constructing a faster RCNN architecture and accomplishing a training;

inputting the polarization image into the faster RCNN architecture accomplished the training to identify the polarization image, and outputting the image with the marked vulnerable plaques; and feed backing the image with the marked vulnerable plaques to the terminal device;

wherein the step of transforming the angiocarpy image in an original Cartesian coordinate system into a polar coordinate system to form a polarization image further comprising:

setting a centre of the angiocarpy image as an origin;

setting an anticlockwise direction as a positive direction, and a direction below the positive direction of the origin as a direction of θ at 0 degree;

obtaining each pixel $T(θ,ρ)$ in the angiocarpy image; θ represents an angle between the pixel and the positive direction, and ρ represents a distance between the pixel and the origin; and calculating coordinate values x, y of each pixel in the angiocarpy image under the polar coordinate system by formulas $x=ρ \cos θ$, $y=ρ \sin θ$.

10. The non-transitory computer readable medium of claim 9, wherein before the step of inputting the polarization image into the faster RCNN architecture accomplished the training to identify the polarization image further comprising:

copying and connecting the polarization image in a horizontal manner, which cause the vulnerable plaques to be reconnected a complete region in the image.

11. The non-transitory computer readable medium of claim 9, wherein the step of constructing a faster RCNN architecture and accomplishing a training comprising:

extracting features to form feature image;

generating proposal region frames on the feature image; and extracting features in the proposal region frames to obtain locations and deep features of the vulnerable plaque.

12. The non-transitory computer readable medium of claim 11, wherein the step of forming anchors on the feature image comprising:

generating the proposal region frames by the nine anchors on different combinations of three different areas and three different ratios.

* * * * *